United States Patent [19]

Cipolletti

[11] Patent Number: 5,674,223

[45] Date of Patent: Oct. 7, 1997

[54] INSTRUMENT FOR IMPLANTING A FEMORAL KNEE PROSTHESIS

[75] Inventor: George B. Cipolletti, Wilton, Conn.

[73] Assignee: Joint Medical Products Corporation, Stamford, Conn.

[21] Appl. No.: 456,083

[22] Filed: May 31, 1995

Related U.S. Application Data

[62] Division of Ser. No. 197,405, Feb. 16, 1994, abandoned.

[51] Int. Cl.$^6$ ................................................. A61B 17/56
[52] U.S. Cl. ................................................. 606/85; 606/88
[58] Field of Search .................................. 606/85, 84, 80, 606/79, 88, 87, 89, 96, 99, 100, 102, 86, 62; 623/18, 20

[56] References Cited

U.S. PATENT DOCUMENTS

| | | | |
|---|---|---|---|
| 4,474,177 | 10/1984 | Whiteside | 606/88 X |
| 4,487,203 | 12/1984 | Androphy | 606/88 X |
| 5,037,423 | 8/1991 | Kenna | 606/88 |
| 5,053,037 | 10/1991 | Lackey . | |
| 5,135,529 | 8/1992 | Paxson et al. . | |
| 5,147,408 | 9/1992 | Noble et al. | 623/23 |
| 5,179,915 | 1/1993 | Cohen et al. | 606/62 |
| 5,190,550 | 3/1993 | Miller et al. . | |
| 5,234,433 | 8/1993 | Bert et al. | 606/88 |
| 5,261,915 | 11/1993 | Durlacher et al. . | |
| 5,350,380 | 9/1994 | Goble et al. | 606/80 |
| 5,387,216 | 2/1995 | Thornhill et al. | 606/88 |

FOREIGN PATENT DOCUMENTS

| | | | |
|---|---|---|---|
| 296986 | 12/1988 | European Pat. Off. | 606/85 |

OTHER PUBLICATIONS

DePuy's product brochure entitled "LCS® Hip System," DePuy, Warsaw, Indiana, 1991.

Joint Medical Products Corporation's product brochure entitled "S-ROM™ Total Knee System, Noiles™ Modular Rotating Hinge Knee, Modular Component Selection Guide," Joint Medical Products Corporation, Stamford, Connecticut, 1991.

Joint Medical Products Corporation's product brochure entitled "S-ROM® Modular Total Knee System," Joint Medical Products Corporation, Stamford, Connecticut, 1993.

Primary Examiner—Guy V. Tucker
Attorney, Agent, or Firm—Maurice M. Klee

[57] ABSTRACT

Instrumentation is provided for forming a cavity in the distal femur and for using that cavity as a reference for making exterior distal cuts of the femoral bone. At least a part of the walls of the cavity are formed by the cortical (hard) bone of the femur. In addition to its use in cutting the exterior bone, the cavity also serves to affix a femoral knee prosthesis to the femoral bone.

10 Claims, 3 Drawing Sheets

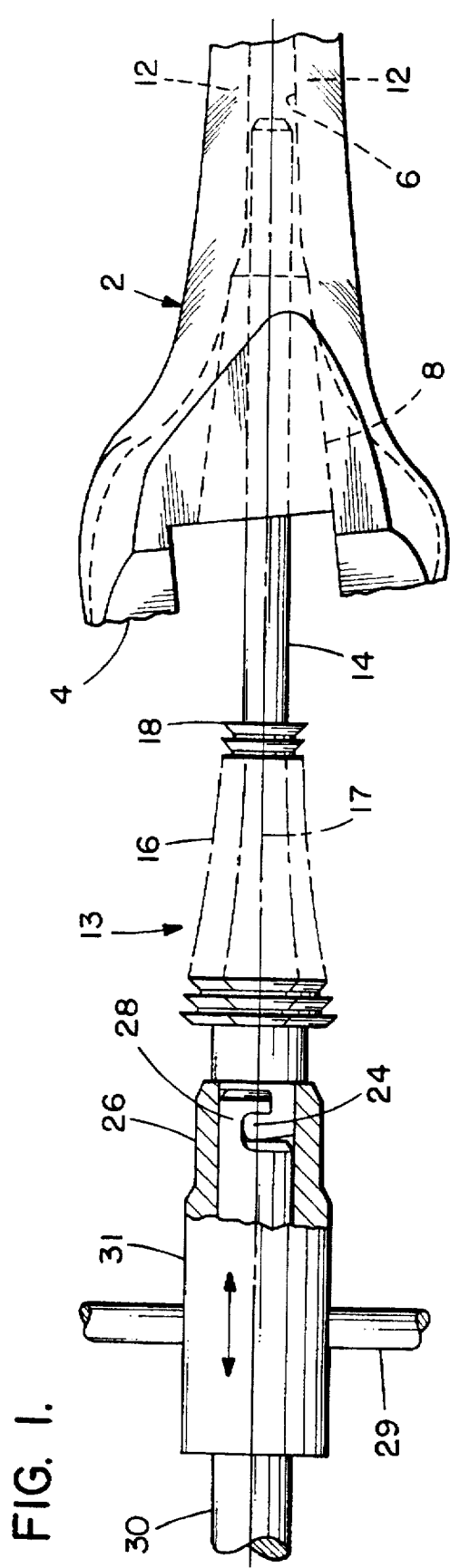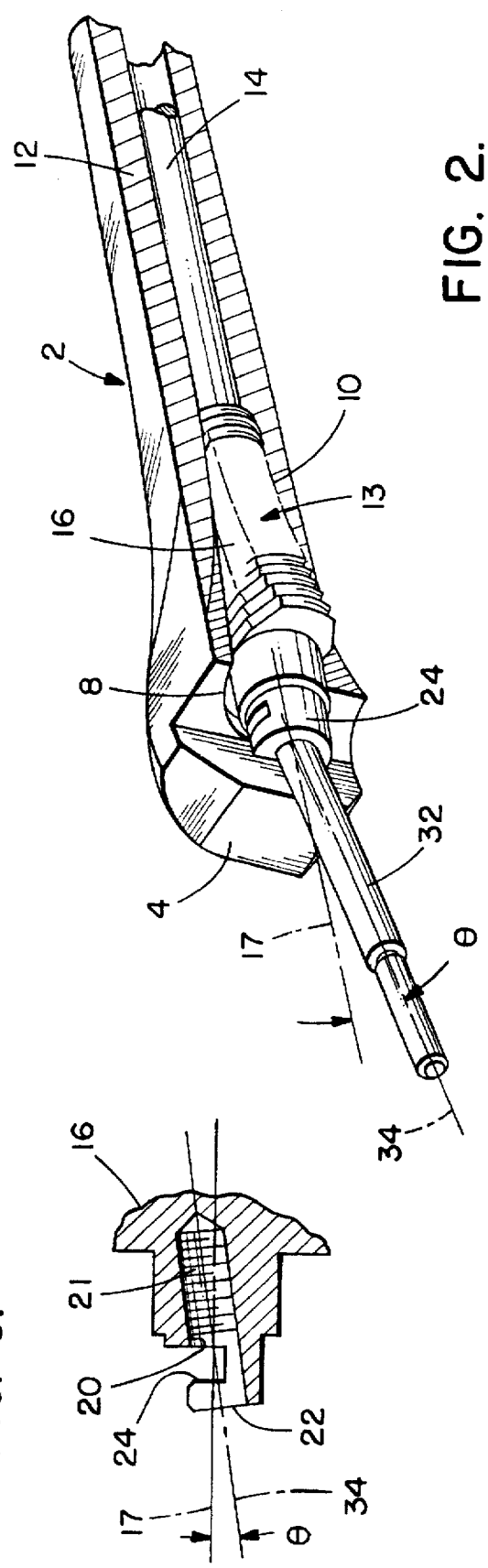

INSTRUMENT FOR IMPLANTING A FEMORAL KNEE PROSTHESIS

This application is a divisional application of application Ser. No. 08/197,405 filed on Feb. 16, 1994, now abandoned.

FIELD OF THE INVENTION

This invention relates to an instrument for shaping the distal end of a patient's femur bone so that it can receive a femoral component of a knee replacement prosthesis and, in particular, to an instrument for use in revision surgery, as opposed to primary surgery, of a femoral knee joint.

BACKGROUND OF THE INVENTION

Numerous instruments have been proposed for use in shaping the distal end of a patient's femur bone during knee replacement surgery. Examples of such instruments are shown in Whiteside, U.S. Pat. No. 4,474,177, and Lackey, U.S. Pat. No. 5,053,037.

The prior art instruments have been designed for use with patients who have a substantial amount of bone at the distal femur which can be used in locating and supporting the instrument during the shaping operation. Such patients generally include those undergoing a primary surgery and, in some cases, those undergoing revision surgery.

For example, as shown in FIG. 16 of the Whiteside patent, blades 34 of intermedullar rod 30 are designed to engage a substantial body of central cancellous bone at the distal end of the patient's femur. Similarly, as shown in FIG. 1 of the Lackey patent, flange 21 of guide 11 is designed to be mounted on the anterior ledge of the patient's distal femur using openings 22.

In many revision cases, the bone at the distal femur is missing or of such poor quality that orientation and stabilization of prior art instruments of the foregoing types is either difficult or impossible to achieve. In addition, there is often insufficient or inadequate bone to support a conventional, externally-mounted, femoral knee prosthesis. As patients have used knee prostheses for longer periods of time and under more strenuous conditions, revision cases of this type have and will continue to become more numerous.

The state of the art in this regard was recently summarized by J. David Blaha, M.D., of the West Virginia University Medical School at the *Ninth Annual Current Concepts in Joint Replacement Conference*, Orlando, Fla., Dec. 16-18, 1993. After explaining how he often uses a femoral knee prosthesis having an elongated stem to gain some reference for the preparation of the distal femur bone, i.e., to "guess" where the final prosthesis should go, Dr. Blaha said: "I think the revision instruments for knee replacement are very poor."

SUMMARY OF THE INVENTION

In view of the foregoing state of the art, it is an object of the present invention to provide an improved instrument and method for preparing the distal end of a patient's femur for receiving a femoral knee prosthesis or a component thereof. More particularly, it is an object of the invention to provide such an instrument and method for use with patients who have an inadequate amount of sound bone at the distal end of the femur.

To achieve the foregoing and other objects, the invention in accordance with certain of its aspects provides a method for preparing the distal end of a patient's femur bone for receiving a femoral knee prosthesis or a component thereof comprising:

(a) forming a longitudinal hole in the femur bone from the distal end thereof;

(b) forming a cavity in the femur bone at its distal end for receiving the femoral knee prosthesis or the component thereof, said cavity communicating with the longitudinal hole and having a cross-sectional area which is larger than that of the longitudinal hole; and (c) shaping the outer surface of the distal end of the femur bone using a cutting guide whose position is established using the cavity as a reference.

In accordance with others of its aspects, the invention provides an instrument for holding a guide, e.g., a cutting or drilling guide, for use in, for example, practicing the above method, wherein the instrument comprises:

a) a first shaft for engagement with the longitudinal hole, the first shaft defining an axis;

b) a body for engagement with the cavity, the body having first and second ends, the first end being connected to the first shaft; and c) means associated with the second end of the body for mounting the guide so that the angle between the axis and a normal to a plane defined by the guide is between about 4 and about 10 degrees.

For some applications, a longitudinal hole and a first shaft are not required, and just a cavity in the bone and an instrument body for engaging the cavity are used.

In either case, the cavity preferably has a shape (referred to herein as the "hard bone shape") which generally corresponds to the shape of the inner surface of the hard bone in the region of the distal end of the femur bone. Also, the instrument body preferably has an outer envelope whose shape is the hard bone shape, i.e., the shape of the body's envelope is substantially the same as that of the cavity. Similarly, the shape of the outer envelope of the femoral knee prosthesis or the component thereof which is to be implanted is the hard bone shape. In this way, the cavity, the instrument body, and the prosthetic device have a physiologically determined common shape whereby the fit and location of the prosthetic device in the patient's femur bone is optimized.

In further preferred embodiments, the outer surface of the instrument body includes cutting means which are used to prepare the cavity, e.g., the body preferably serves as a broach for preparing the cavity. In this way, the desired common shape of the cavity-body-prosthetic device is immediately established upon the formation of the cavity. Moreover, for these preferred embodiments wherein the instrument body includes cutting means, the drilling and cutting guides can be mounted on the body and shaping of the bone commenced without the need to remove the body from the bone. This significantly streamlines the bone preparation procedure for the distal femur.

BRIEF DESCRIPTION OF THE DRAWINGS

FIG. 1 is an anterior-posterior view of the distal end of a left femur showing the apparatus of the invention during insertion into the bone.

FIG. 2 is a perspective view, partially in section, showing the apparatus fully seated in the distal end of the femur bone of FIG. 1.

FIG. 3 is an expanded, cross-sectional view of the distal end of the body portion of the apparatus of the invention.

Figure 4:
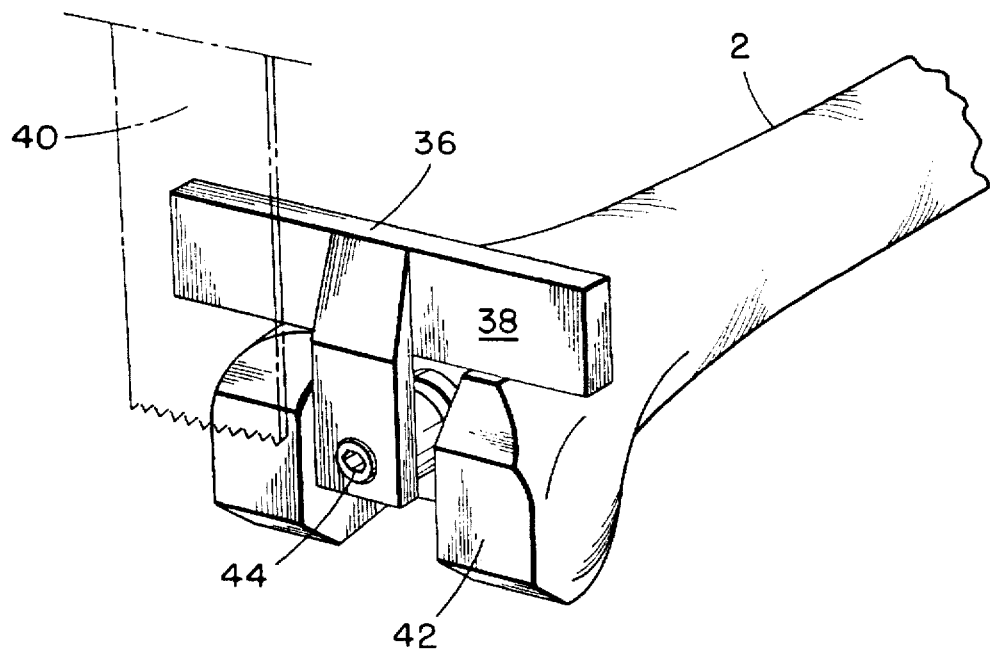
FIG. 4 is a perspective view showing a first cutting guide mounted on the apparatus of the invention.
Figure 5:
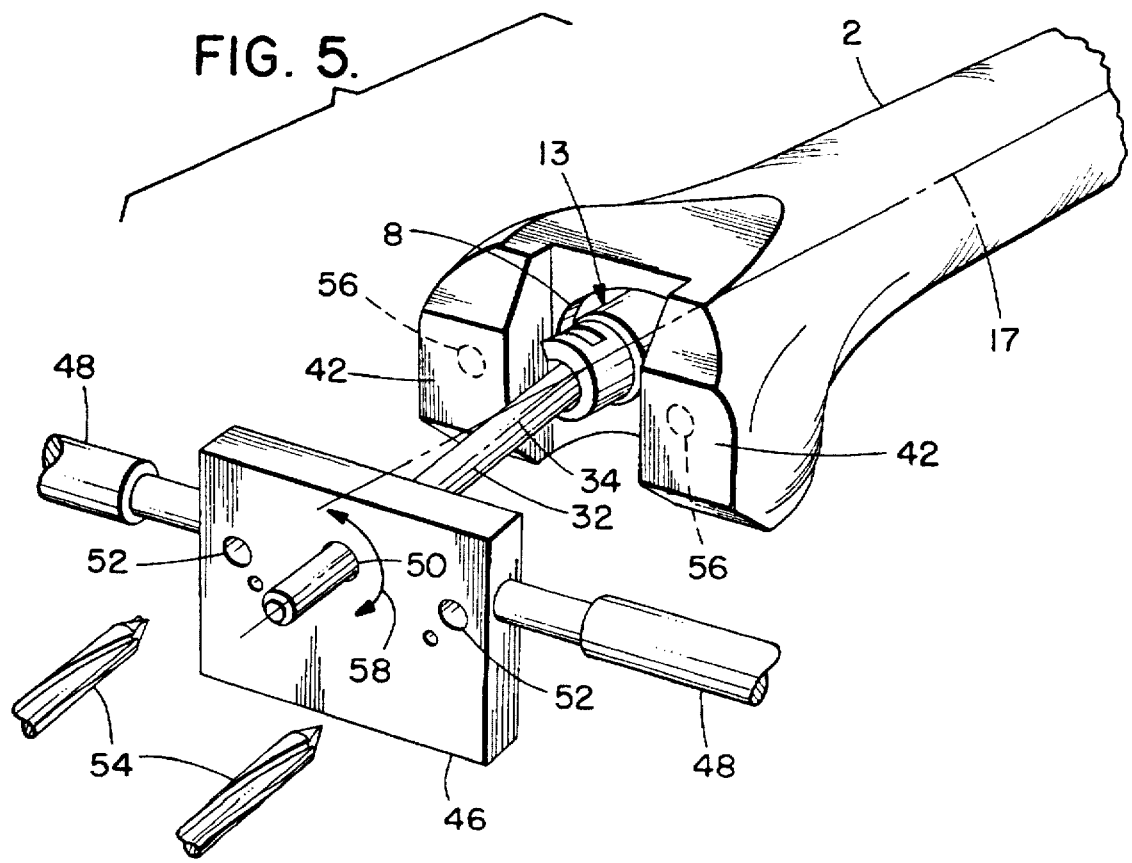
FIG. 5 is a perspective view showing a drill guide mounted on the apparatus of the invention.

The foregoing drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

The reference numbers used in the drawings correspond to the following:

| 2 | femur bone |
|---|---|
| 4 | distal end of femur bone |
| 6 | straight hole in femur bone |
| 8 | conical hole in femur bone |
| 10 | cavity in femur bone which has the hard bone shape |
| 12 | hard bone in the region of the distal end of the femur bone |
| 13 | instrument |
| 14 | instrument pilot (first shaft) |
| 16 | instrument body |
| 17 | longitudinal axis of pilot 14, body 16, and femur bone 2 |
| 18 | cutting teeth on body 16 |
| 20 | hole in body 16 |
| 21 | thread in hole 20 |
| 22 | oblique surface on body 16 |
| 24 | jaw of body 16 for attaching driver 26 |
| 26 | driver |
| 28 | driver jaw |
| 29 | driver studs |
| 30 | driver handle |
| 31 | retractable sleeve of driver |
| 32 | instrument pin |
| 34 | normal to surface 22 and center line of pin 32 and hole 20 |
| 36 | distal cutting guide |
| 38 | guide surface of distal cutting guide 36 |
| 40 | oscillating saw blade |
| 42 | distal surface of femur bone |
| 44 | screw |
| 46 | drill guide plate |
| 48 | handles |
| 50 | center hole in drill guide plate 46 |
| 52 | drill guide holes in drill guide plate 46 |
| 54 | drills |
| 56 | rotational alignment holes in distal surface 42 |
| 58 | rotational arrow |
| 60 | cutting guide |
| 62 | center alignment hole in cutting guide 60 |
| 64 | alignment pins of cutting guide 60 |
| 66 | saw guide |
| 68 | saw guide pins |
| 70 | saw guide holes in cutting guide 60 |
| 72 | anterior surface of cutting guide 60 |
| 74 | posterior surface of cutting guide 60 |
| 76 | chamfer cutting slots of cutting guide 60 |
| 78 | posterior saw guide slots of cutting guide 60 |

DESCRIPTION OF THE PREFERRED EMBODIMENTS

FIG. 1 shows the distal end 4 of femur bone 2 from which a prior prosthesis has been removed. As a first step in the preparation of this bone to receive a revision prosthesis, hole 6 has been cut into the femur using, for example, a straight reamer. Also, a larger conical hole 8 has been formed in the bone using a conical reamer which preferably has a pilot which fits into hole 6.

Also shown in FIG. 1 is the instrument of the invention in its configuration for use in forming a cavity 10 which has the hard bone shape (see FIG. 2). Instrument 13 comprises removable pilot 14 and body 16. Pilot 14 is designed to slidably engage with straight hole 6. It can be attached to body 16 in various ways, including by means of a screw thread.

Figure 8:
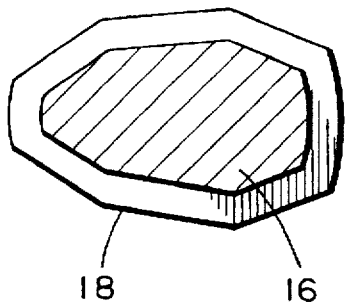
FIG. 8 is a cross-sectional view along lines 8—8 in FIG. 7 of the body of the apparatus.

The outer surface of body 16 includes cutting teeth 18 so that the body can serve as a broach. Representative cutting teeth are shown in the figures. In practice, the teeth preferably cover the entire outer surface of the body except for the ends. The envelope of these teeth has a shape which generally corresponds to the hard bone shape. The cross-section of the hard bone shape in the distal region of the femur is generally that of a longitudinal section through an egg, i.e., the cross-section is "egg shaped", with the large end of the longitudinal section being lateral. As shown in FIG. 8, the cross-section of body 16 has such an egg shape.

In practice, a series of instruments 13 is provided to the surgeon having a range of cross-sectional dimensions and body lengths. The series is usable with either the right or left femur. In preparing conical hole 8, the surgeon takes into account the instrument 13 which he or she expects to use and selects a conical reamer and depth of reaming appropriate to the chosen instrument. As part of this decision, the surgeon also must consider the desired final leg length. Instruments 13 and/or the conical reamer can include graduations to assist the surgeon in this decision.

At its distal end, body 16 includes jaw 24 for engaging jaw 28 of driver 26 (see FIG. 3). This end of the body also includes oblique surface 22 and hole 20, which has an internal screw thread 21. As discussed below, hole 20 receives pin 32. As shown in, for example, FIG. 2, the longitudinal axis 17 of body 16 and the centerline 34 of pin 32 intersect at an angle θ, which preferably is in the range of from about 4° to about 10°. As shown in, for example, FIG. 3, the normal 34 to oblique surface 22 also intersects longitudinal axis 17 at the angle θ.

Driver 26 includes spring-loaded, retractable sleeve 31 which is operated by studs 29. The spring-loaded sleeve forces driver jaw 28 into engagement with body jaw 24 so that cutting teeth 18 can be driven into femur bone 2 by striking the end of handle 30 (not shown) with a mallet. This driving of the cutting teeth into the bone produces cavity 10 having the hard bone shape.

Once the driving has been completed, sleeve 31 of driver 26 is retracted so as to disengage jaw 28 of the driver from jaw 24 of the body. Thereafter, the remaining steps in the bone shaping procedure are performed without removing body 16 from cavity 10.

By leaving body 16 in place, the locations of all external bone cuts are determined from the internal cavity 10, a result not previously achievable in the art. This results in a superior fit of both the internal and external aspects of the femoral prosthesis with the prepared surfaces of the femur bone, in comparison with the fit achieved with prior techniques. In particular, a high level of fit is achieved for the internal aspects of the prosthesis with the hard cortical bone 12 of the femur, which is the strongest bone in the distal region of the femur.

The remaining steps in the bone shaping procedure involve mounting a sequence of guides onto instrument 13 and using those guides in accurately cutting the bone to correspond to the bone engaging surfaces of the prosthetic device. FIG. 4 shows a distal cutting guide 36 having a surface 38 against which saw 40 is placed during cutting of surface 42 in femur bone 2. Guide 36 is clamped against surface 22 of instrument 13 by means of screw 44 which engages screw thread 21 in hole 20. In this way, guide 36 is oriented at the angle θ with respect to the longitudinal axis 17 of femur bone 2, i.e., the plane of guide 36 defined for example by the plane of surface 38 is oriented at the angle θ with respect to axis 17 in that θ is the angle between a normal to the plane and axis 17.

Once surface 42 has been prepared, guide 36 is removed and pin 32 is screwed into hole 20. Drill guide plate 46 is then mounted onto pin 32 by means of center hole 50 and located against surface 42 by means of handles 48. Center hole 50 is normal to the proximal and distal faces of guide 46 so that the plate is oriented at the angle θ relative to axis 17. Plate 46 is rotationally aligned as shown by arrow 58 based on the anatomical configuration of the remaining bone of the patient's distal femur. Once aligned, rotational alignment holes 56 are formed in surface 42 using drills 54 which pass through drill guide holes 52 in plate 46.

Figure 6:
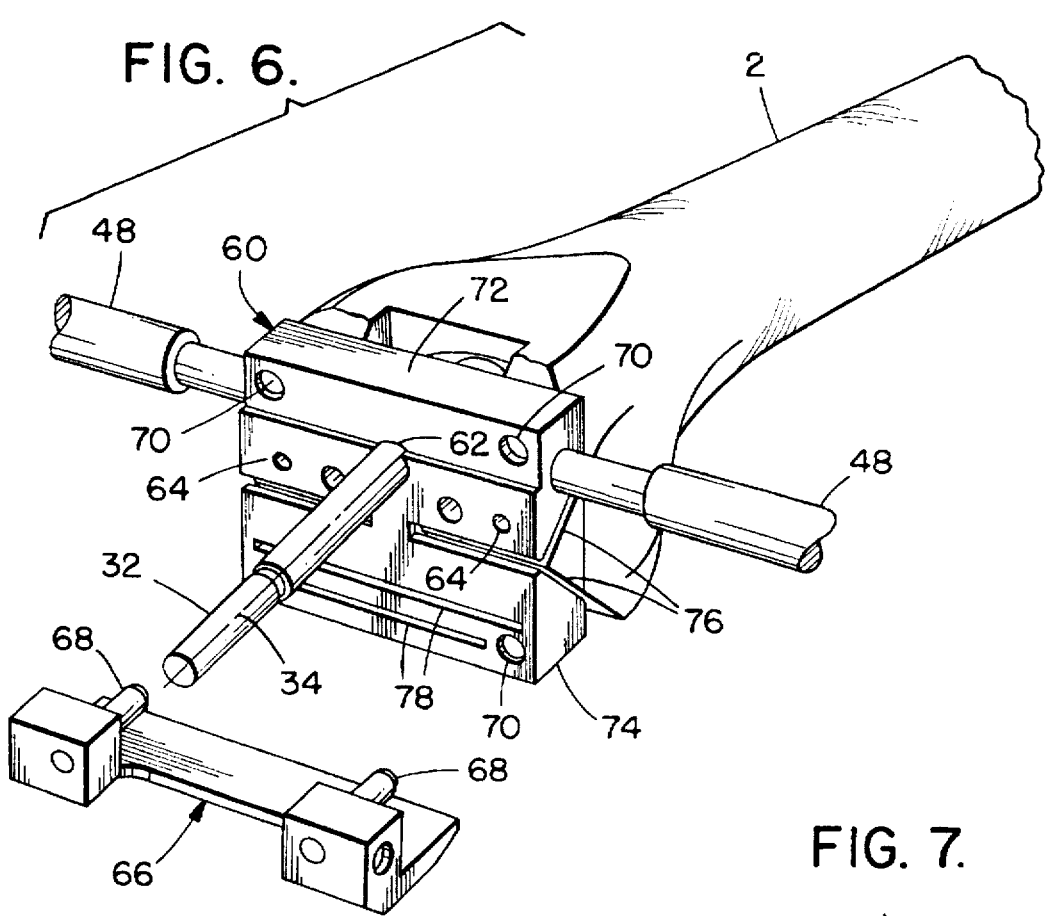
FIG. 6 is a perspective view showing a second cutting guide mounted on the apparatus of the invention.

Drill guide plate 46 is then removed and replaced with cutting guide 60. Guide 60 includes center alignment hole 62 which is passed over pin 32 and alignment pins 64 which engage holes 56 in distal surface 42 of the patient's femur. As in the case of hole 50 of guide 46, hole 62 of guide 60 is normal to the guide's proximal and distal faces so that the guide is oriented at the angle θ relative to axis 17. The location of the distal ends of alignment pins 64 are shown in FIG. 6. The pins themselves extend proximally from the proximal surface of cutting guide 60. Additional fixation pins (not shown) can be used to further stabilize cutting guide 60 on the end of the femur. Handles 48 are used in this mounting and alignment procedure.

Once cutting guide 60 has been secured in place, pin 32 can be removed if desired by the surgeon. Thereafter, cuts are sequentially made using the anterior and posterior surfaces 72,74 of guide 60 to guide an appropriate saw. Saw guide 66, which can be mounted on cutting guide 60 in two positions through the engagement of pins 68 with holes 70, can be used to stabilize the saw during the making of these cuts. Posterior saw guide slots 78 formed in the body of guide 60 can be used to make the posterior cut in cases where the patient is missing substantial amounts of posterior bone.

Finally, anterior and posterior chamfer saw cuts are made using slots 76. Thereafter, cutting guide 60 is removed, pin 32, if not previously removed, is removed, and driver 26 is reattached to instrument 13 and used to extract the instrument from the patient's bone. The bone is then ready to receive the prosthetic device. As discussed above, the prosthetic device has the hard bone shape so as to form a strong union with cavity 10. The prosthetic device also has other surfaces which engage the outer surfaces of the distal femur prepared in accordance with the above procedure. In this way, the desired high level of accurate fixation of the prosthesis is achieved.

Figure 7:
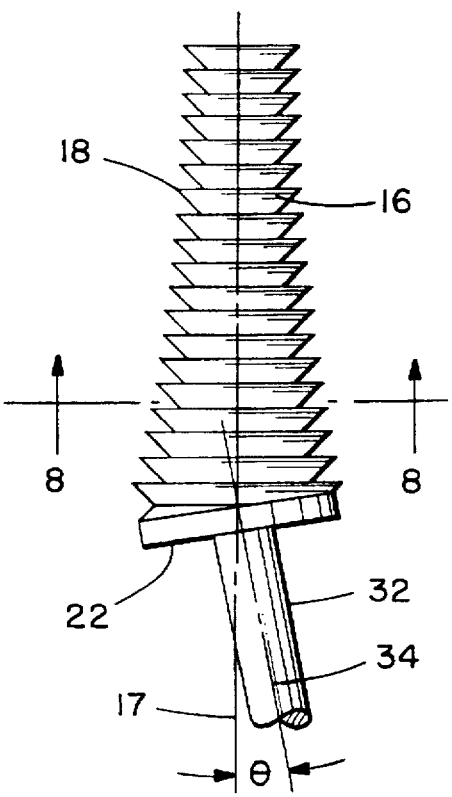
FIG. 7 is a schematic diagram of an alternate embodiment of the apparatus of the invention which does not include a first shaft.

FIG. 7 shows an alternate embodiment of instrument 13 which comprises just body 16, i.e., it does not include pilot 14. This embodiment can be used in the same manner as that of FIGS. 1–6 except that straight hole 6 is not formed in the femur. The embodiment can be employed where, for example, the patient has a hip prosthesis which extends distally in the femoral canal to a point where a straight hole 6 cannot effectively be formed in the distal end of the femur.

FIG. 8 shows the cross-sectional profile of body 16 of the prosthesis of FIG. 7. As discussed above, this profile is egg-shaped with the large end of the egg being lateral. The body 16 of the prosthesis of FIGS. 1–6 has the same cross-section.

Instrument 13 and its associated components are fabricated using conventional techniques employed in the manufacture of surgical instruments. Similarly, the instrument is composed of conventional stainless steels or other materials used in constructing surgical instruments.

Although preferred and other embodiments of the invention have been described herein, other embodiments may be perceived by those skilled in the art without departing from the scope of the invention as defined by the following claims.

What is claimed is:

1. A method for preparing the distal end of a patient's femur bone for receiving a femoral knee prosthesis or a component thereof, said femoral knee prosthesis or component thereof having a three dimensional outer envelope a portion of which has a shape which generally corresponds to the inner surface of the hard bone in the region of the distal end of the femur, said portion having a longitudinal axis and a cross-section transverse to said longitudinal axis whose perimeter is substantially egg shaped:

said method comprising:
   (a) forming a longitudinal hole in the femur bone from the distal end thereof;
   (b) forming a cavity in the femur bone at its distal end for receiving the femoral knee prosthesis or the component thereof, said cavity:
      (i) communicating with the longitudinal hole;
      (ii) having a cross-sectional area which is larger than that of the longitudinal hole; and
      (iii) having a three dimensional outer envelope at least a portion of which has a shape which generally corresponds to the inner surface of the hard bone in the region of the distal end of the femur, said portion having a longitudinal axis and a cross-section transverse to said longitudinal axis whose perimeter is substantially egg shaped; and
   (c) shaping the outer surface of the distal end of the femur bone using a cutting guide whose position is established using the cavity as a reference by inserting an instrument into the cavity, said instrument having a three dimensional outer envelope at least a portion of which has a shape which generally corresponds to the inner surface of the hard bone in the region of the distal end of the femur, said portion having a longitudinal axis and a cross-section transverse to said longitudinal axis whose perimeter is substantially egg shaped.

2. The method of claim 1 wherein the instrument comprises a broach which is used in step (b) to form the cavity.

3. A method for preparing the distal end of a patient's femur bone for receiving a femoral knee prosthesis or a component thereof, said femoral knee prosthesis or component thereof having a three dimensional outer envelope a portion of which has a shape which generally corresponds to the inner surface of the hard bone in the region of the distal end of the femur said portion having a longitudinal axis and a cross-section transverse to said longitudinal axis whose perimeter is substantially egg shaped;

said method comprising:
   (a) forming a cavity in the femur bone at its distal end for receiving the femoral knee prosthesis or the component thereof, said cavity having a three dimensional outer envelope at least a portion of which has a shape which generally corresponds to the inner surface of the hard bone in the region of the distal end of the femur, said portion having a longitudinal axis and a cross-section transverse to said longitudinal axis whose perimeter is substantially egg shaped; and (b) shaping the outer surface of the distal end of the femur bone using a cutting guide whose position is established using the cavity as a reference by inserting an instrument into the cavity, said instrument having a three dimensional outer envelope at least a portion of which has a shape which generally corresponds to the inner surface of the hard bone in the region of the distal end of the femur said portion having a longitudinal axis and a cross-section transverse to said longitudinal axis whose perimeter is substantially egg shaped.

4. The method of claim 3 wherein the instrument comprises a broach which is used in step (a) to form the cavity.

5. A method for preparing the distal end of a patient's femur bone for receiving a femoral knee prosthesis or a component thereof comprising:

(a) forming a longitudinal hole in the femur bone from the distal end thereof;

(b) by means of a broach, forming a cavity in the femur bone at its distal end for receiving the femoral knee prosthesis or the component thereof, said cavity communicating with the longitudinal hole and having a cross-sectional area which is larger than that of the longitudinal hole; and (c) without removing the broach, shaping the outer surface of the distal end of the femur bone using a cutting guide whose position is established using the broach as a reference.

6. The method of claim 5 wherein at least a portion of the inner surface of the cavity comprises cortical bone.

7. The method of claim 6 wherein the shape of the cavity generally corresponds to the shape of the inner surface of the cortical bone in the region of the distal end of the femur.

8. The method of claim 5 wherein the broach has an outer envelope the shape of at least a portion of which is substantially the same as the shape of a portion of the outer envelope of the femoral knee prosthesis or the component thereof.

9. A method for preparing the distal end of a patient's femur bone for receiving a femoral knee prosthesis or a component thereof comprising:

(a) by means of a broach, forming a cavity in the femur bone at its distal end for receiving the femoral knee prosthesis or the component thereof, said cavity having a shape which generally corresponds to the shape of the inner surface of the hard bone in the region of said distal end; and (b) without removing the broach, shaping the outer surface of the distal end of the femur bone using a cutting guide whose position is established using the broach as a reference.

10. The method of claim 9 wherein the broach has an outer envelope the shape of at least a portion of which is substantially the same as the shape of a portion of the outer envelope of the femoral knee prosthesis or the component thereof.

* * * * *